United States Patent [19]

Gernet et al.

[11] Patent Number: 5,730,298

[45] Date of Patent: Mar. 24, 1998

[54] PROCESS FOR REMOVING RETURNABLE BOTTLES FROM CIRCULATION

[75] Inventors: Pierre Gernet, Ennetbaden; Daniel Jungo, Würenlos, both of Switzerland

[73] Assignee: Elpatronic AG, Zug, Switzerland

[21] Appl. No.: 642,592

[22] Filed: May 3, 1996

Related U.S. Application Data

[63] Continuation of Ser. No. 316,789, Sep. 30, 1994, abandoned.

[30] Foreign Application Priority Data

Oct. 8, 1993 [CH] Switzerland .......... 03 045/93

[51] Int. Cl.$^6$ .................. B07C 5/00; G01N 21/00
[52] U.S. Cl. .................. 209/524; 209/587; 209/599;
209/938; 250/223 B; 250/559.36; 356/240;
356/359
[58] Field of Search .................. 209/522, 523,
209/524, 525, 526, 576, 579, 587, 599,
938; 250/223 B, 562, 563, 559.36, 572;
356/239, 240, 241, 259, 360

[56] References Cited

U.S. PATENT DOCUMENTS

| | | |
|---|---|---|
| 4,591,996 | 5/1986 | Vachon .................. 356/360 X |
| 4,707,610 | 11/1987 | Lindow et al. .......... 250/563 X |
| 4,903,528 | 2/1990 | Balakrishnan et al. ... 250/563 X |
| 5,127,726 | 7/1992 | Moran .................... 250/572 X |
| 5,233,199 | 8/1993 | Toyama ................. 250/223 R X |
| 5,405,015 | 4/1995 | Bhatia et al. ........... 209/526 X |

FOREIGN PATENT DOCUMENTS

| | | |
|---|---|---|
| 2087396 | 7/1993 | Canada . |
| 0 555 646 | 8/1993 | European Pat. Off. . |
| 3611 536 | 10/1987 | Germany . |
| 278740 | 12/1986 | Japan .................. 250/223 B |

OTHER PUBLICATIONS

Japanese Patent Abstract, vol. 6, No. 75 (P–114), May 12, 1982, No. JP–A–57 013 342 (Kirin Brewery) Jan. 23, 1982.

Primary Examiner—Tuan Nguyen
Attorney, Agent, or Firm—McCormick, Paulding & Huber

[57] ABSTRACT

To determine whether stress cracks are present in the bottom area of a plastic bottle which make it unfit for further use, the bottle bottom is scanned in the potential crack region by the measuring beam of a laser distance-measuring instrument. From its output signal, the prevalence and depth of the cracks can be identified sufficiently to enable a decision to be made on the removal of the bottle from circulation.

7 Claims, 3 Drawing Sheets

PROCESS FOR REMOVING RETURNABLE BOTTLES FROM CIRCULATION

This is a continuation of application Ser. No. 08/316,789 filed on Sep. 30, 1994, now abandoned.

BACKGROUND OF THE INVENTION

The invention relates to a process for removing returnable bottles, in particular returnable plastic bottles, from circulation. The invention also relates to a device for carrying out the process.

With returnable plastic bottles in particular, eg. PET bottles, which have a limited life, the problem arises that bottles coming to the end of their life owing to so-called stress cracks need to be promptly taken out of circulation, not only to ensure that bottles are not fractured or split while in use by the consumer, but also to avoid splitting or bursting of bottles in the bottling plant during the refilling operation, in the course of which the individual bottle is subjected to relatively high pressure. Until now no way has been found of detecting the usual fatigue damage of such bottles (appearing especially in the form of fine, more or less deep, cracks) in such a way that the end of the bottle's life can be reliably identified.

The object, therefore, is to make it possible to remove bottles from circulation promptly before they reach the end of their service life, by reliably detecting stress cracks, but without taking bottles out of circulation unduly prematurely.

SUMMARY OF THE INVENTION

According to the invention this object is attained by conveying the bottles past an optical distance-measuring instrument essentially upon every bottle-return, so that the measuring beam of the instrument scans the rim area of the bottom of the bottle and in that the distance measurement signal is evaluated and the individual bottles are each removed from circulation or left in circulation according to the outcome of the evaluation.

It has been found that with an optical distance-measuring instrument, in particular with a laser distance-measuring instrument, it is possible to obtain a distance measurement signal containing interpretable information on the quantity and depth of the stress cracks even when the bottles are being conveyed at high speed on an industrial conveying system (eg. at 600 bottles per minute), so that the individual bottle can be removed or not removed from circulation as a result of the evaluation of the distance measurement signal. The result is a simple and inexpensive facility for detecting stress cracks.

The luminous intensity of the reflected measuring beam is preferably also included in the evaluation, in order to be able to discriminate even better between bottles classed as "sound" and those classed as "unsound".

BRIEF DESCRIPTION OF THE DRAWINGS

Embodiments of the invention will now be described in detail, by way of example, with reference to the drawings, in which.

BRIEF DESCRIPTION OF THE PREFERRED EMBODIMENTS

Figure 1:
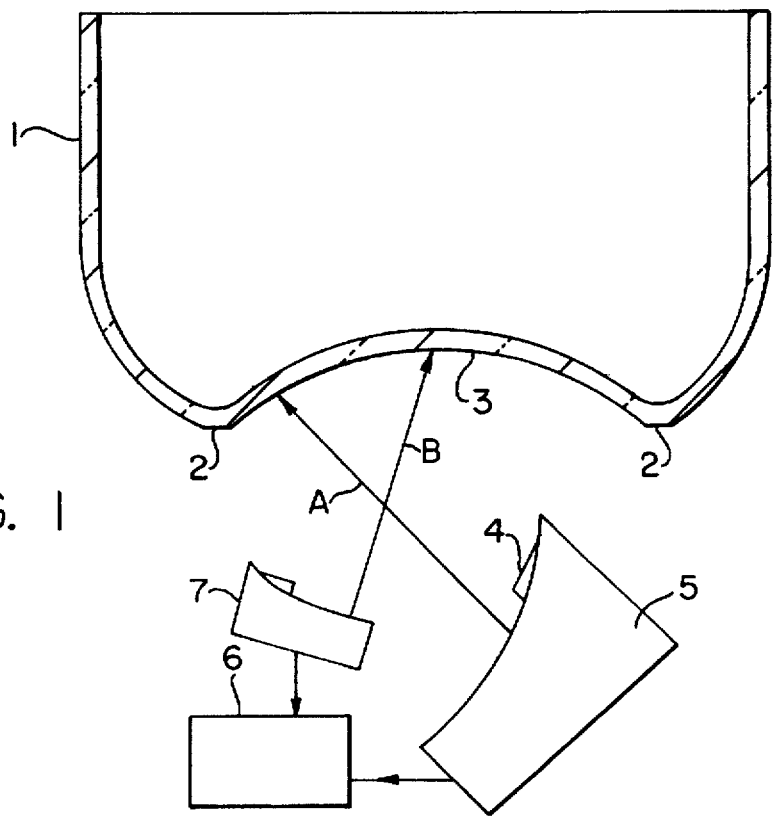
FIG. 1 schematically shows the arrangement of a distance-measuring instrument for scanning the rim area of the bottom of the bottle.
Figure 2:
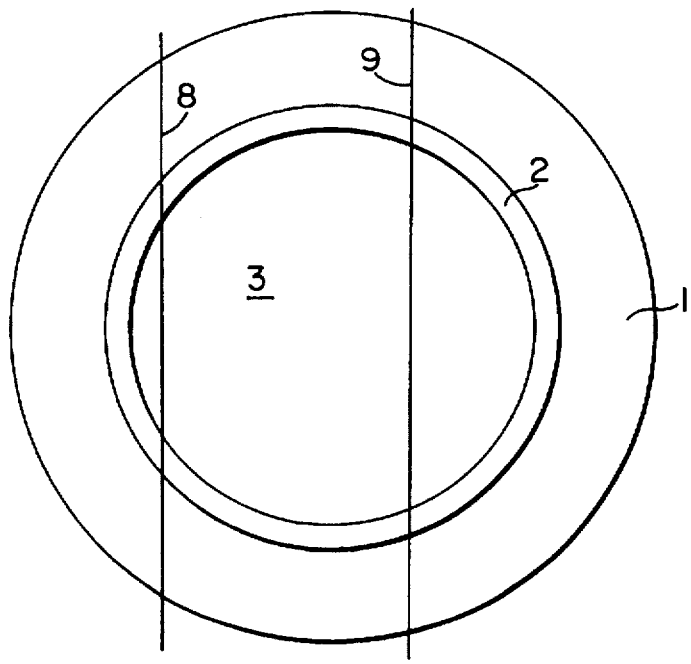
FIG. 2 schematically shows a bottle bottom viewed from below, indicating the line of the measuring beam.

FIG. 1 show in highly schematic form the lower region of a PET bottle 1 (in vertical cross-section). Visible in the figure are the base surface 2 of the bottle and the "dome" 3 etching up from the base surface into the interior of the bottle. The distance-measuring instrument 5, which is eg. an opto NCDT Series 1605 laser distance-measuring instrument made by Micro-Epsilon Messtechnik GmbH & Co KG, Ortenburg, Germany, is arranged at a distance from the bottle as specified by the instrument manufacturer to operate on the known principle of measurement by triangulation. A light spot is projected onto the bottle. A lens 4 images this light spot onto a position sensor in the distance-measuring instrument. The position sensor supplies a position-related analogue output voltage proportional to the measurement path (the distance between sensor and bottle bottom). An additional analogue output voltage represents the reflected luminous intensity. The output voltages are fed to an analysing device 6, for example a computer. When using the distance-measuring instrument for detecting bottles to be removed, the bottle 1 is located on a conveying system not shown in the drawing, eg. on a linear conveyor or a carousel conveyor, and is moved in relation to the distance-measuring instrument. The path 7 of the measuring point extends, eg. as schematically indicated in FIG. 2, beyond the base surface 2 into the inner rim area of the base surface 2 and/or the outer rim area of the dome 3. When the measuring point is at the centre of its path as shown in FIG. 1, the distance between the measuring point and the base surface is preferably approximately 3 to 8 mm and more preferably 5 to 8 mm. The distance-measuring instrument is preferably angled at approximately 45° to the longitudinal axis of the bottle.

An additional distance-measuring instrument 7, similar to the distance-measuring instrument 5 could be used for testing another point on the bottom of the bottle. For example, there could be another path 9, as shown in FIG. 2, parallel with the path 8 shown and on the opposite side; or the path of the second measuring point could extend at an oblique angle to the path shown. It is also possible to hold the measuring point at a fixed point in space and to rotate the bottle about a vertical axis so that the measuring point path is circular. If there are several paths, these can be at different distances from the base surface. Also, the width of the crack ring can be determined with great accuracy if several distance-measuring instruments are used. However, even with a single path the width of the crack ring can be inferred, as will be explained presently with reference to FIGS. 3A and 3B.

Figure 3A:
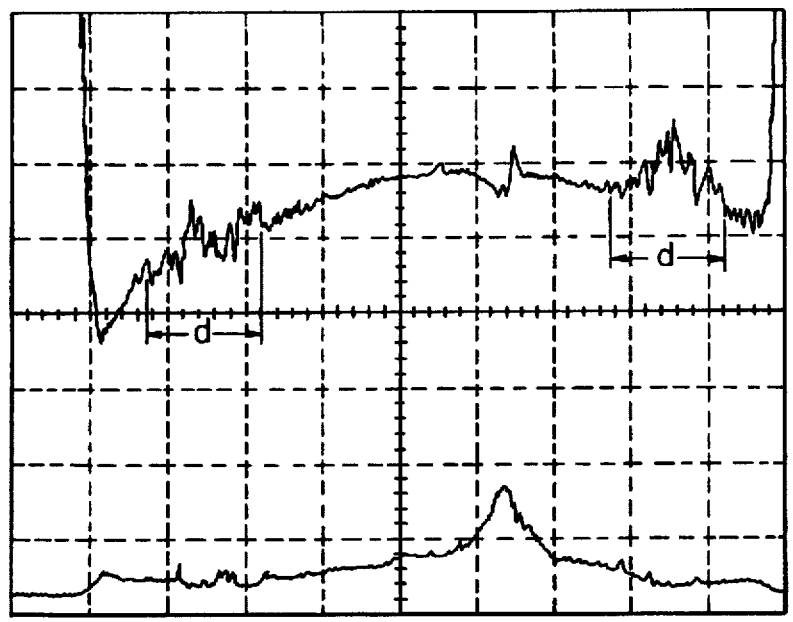
FIG. 3A, FIG. 3B and FIG. 3C show graphs of the distance-measuring instrument output signals for evaluation.
Figure 3B:
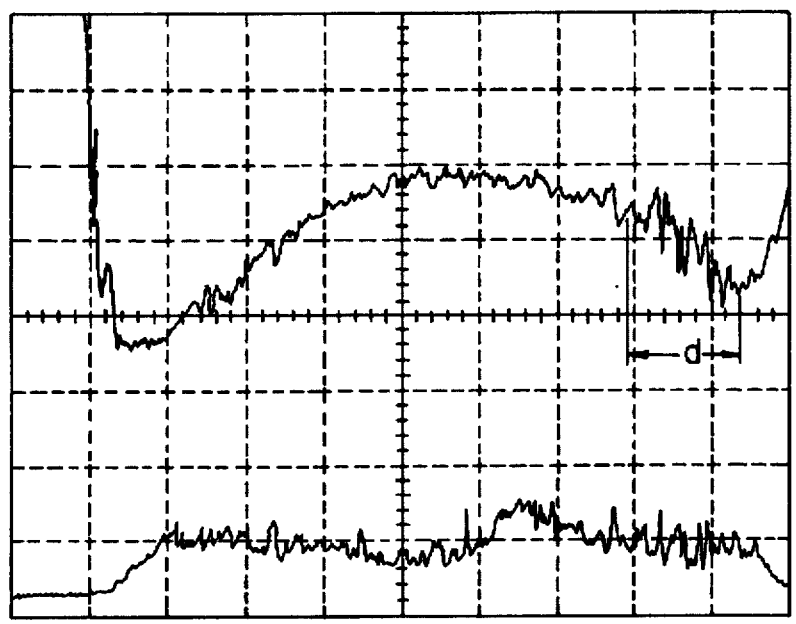
Figure 3C:
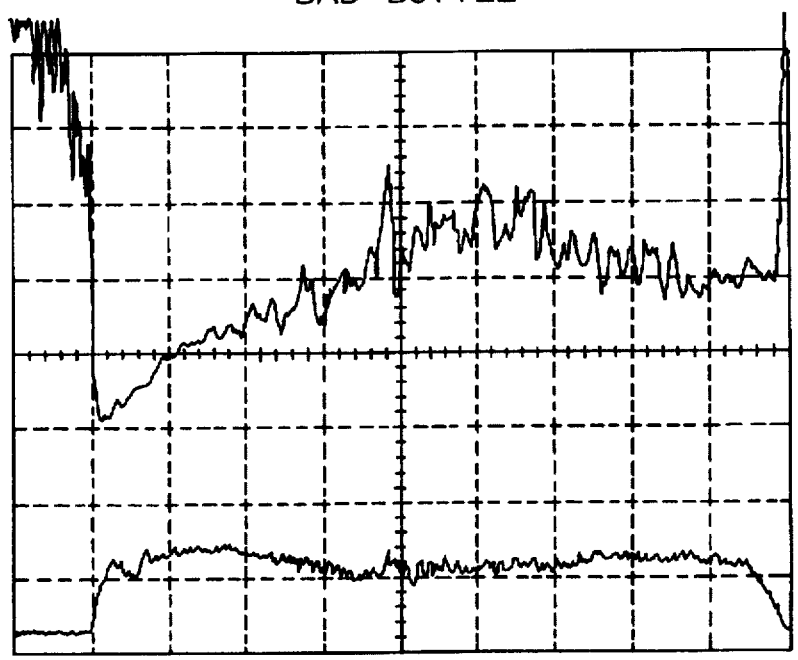

FIGS. 3A, 3B and 3C show output signals of the distance-measuring instrument. All graphs contain two traces. In each case the upper curve shows a measurement signal directly indicating the distance between the bottle and the distance-measuring instrument. The curve shows a surface panorama of the inner dome at a scanning angle of about 45°. The maximum measuring height difference within the dome is about 8 mm. Because of the angle of scanning the dome appears more curved than expected.

The lower curve represents the quantity of light reflected by the measured object. With the aid of this signal the meaningfulness of the sensor can be enhanced. It enables the tested region to be monitored more closely, and valid and invalid signals to be distinguished more clearly.

These recordings were all made with the same mounting and adjustment. Other circumstances may arise with different settings and hence with different scanning planes and angles. The mounting is therefore a determining factor in each case.

For the evaluation of the signals, a number of variants are indicated.

The upper curve shows the relative distance from the sensor to the object. The selected object is the point which reflects most light to the PSD sensor. This means that the background should be screened out, as the back wall is also scanned by the laser beam.

Since the dome is being scanned in a known range, a valid distance-signal must lie in a known band width. If the signal is reflected in another plane, the information can immediately be assumed to be false. This "measuring window" is defined by running through a bottle with a painted bottom and storing this signal. A measuring range which has a programmable band width is then superimposed on this reference signal.

The measuring signal must then necessarily lie in this band width. Owing to variations in the bottle geometry and positional errors of the objects during measurement, the width of the window must be determined and set at the outset.

Signals which lie outside the boundary can be disregarded. The remaining portion of the signals can then be reviewed.

The second signal (lower curve) can then be evaluated by a similar process. This signal corresponds to the quantity of light reflected. If this signal lies within a range (which is adjustable), the reading (upper curve) can be identified as a valid signal. In sound bottles, reflections occur in the central area which produce a typical peak in the lower curve. In highly stressed bottles, however, the lower reading (quantity of light) appears rather more constant. In this signal, typical ripples can additionally be quantified.

Summary of Evaluation Options

Upper curve (distance)
Closeness of match with reference curve (difference)
Ripple amplitudes (crack depth)
Continuity of line (signal jumps)
Zone-evaluation 1 (due to reflection at dome centre)
Zone-evaluation 2 (due to optical distortion caused by scanning)
Distribution of cracks over diameter (width of crack ring)
Frequency analysis
Lower curve (light quantity)
Continuity of reflection (constancy; detection of typical mirroring)
Detection of typical ripples (frequency, amplitude)
Comparison of the two curves
Individual cracks
Haze only (very fine structural change at the surface—looks like condensation)
Evaluate lower and upper limit (acceptable band width; plausibility)
Start/end of detection (dome-synchronization)

A first possibility is to carry out an initial analogue signal processing which highlights some of the listed effects. Thus, the ripple component of both curves can be formed by filtering and processing by means of RMS-DC-converters or differentiation of the signal (by differentiator). Total reflected light power can be summed with an integrator, and evaluated.

A second possibility is to record some measurement curves by means of AD-card. Editing and combination can then be performed by more extensive mathematical methods. These will yield an optimum and flexible evaluation.

The actual interpretation can be confined to spot comparisons of individual points on the graphs obtained with reference values, performed on-line by a computer. This can be done eg. by specifying an upper and lower limit curve for each of the two curves, with these limit curves forming a window for the signal curve. Points where the signal curve lies outside the predetermined window can then be specially evaluated. By suitable evaluation (if need be, using several distance-measuring instruments) it is possible to establish whether a fine roughened surface (haze) is present, or whether many fine cracks or few deep cracks are present. It is also possible to distinguish between radial cracks and circular-arc cracks. Bottles identified as defective are then removed from the conveyor path. It is also possible to make a comparison of the individual graphs obtained with standard curves, using eg. neural networks or "fuzzy logic" systems.

The width of the crack ring can be got from dimension d entered in FIGS. 3A and 3B.

We claim:

1. Process for removing returnable bottles from circulation, comprising the steps of:
   conveying the bottles past an optical distance-measuring instrument upon every bottle-return,
   scanning a line along the exterior of the bottoms of the bottles for cracks using a measuring beam of the optical distance-measuring instrument and sensing the measuring beam as reflected from the line scanned along the exterior of the bottoms to produce distance measurement signals and signals indicative of the intensity of the reflected measuring beam,
   evaluating the distance measurement signals and the reflected measuring beam intensity signals to determine whether or not individual bottles have a predetermined level of cracking, and
   removing the individual bottles from circulation or leaving the individual bottles in circulation according to the outcome of the step of evaluating.

2. Process according to claim 1, wherein during the step of scanning the path of the measuring beam extends in a region of a bottle dome of the bottom of the bottle at a distance of approximately 3 to 8 mm from a base surface of the bottom of bottle.

3. Process according to claim 1, wherein during the step of scanning the distance-measuring instrument scans the bottle bottom at an angle of approximately 45° to a longitudinal axis of each bottle.

4. Process according to claim 1, wherein the step of evaluating includes the steps of:
   plotting the individual distance measurement signals over time, and
   comparing the distance measurement signals with predetermined upper and lower values during the step of evaluating.

5. Process according to claim 1, wherein the step of evaluating includes the steps of:
   plotting the individual beam intensity signals over time and,
   comparing the beam intensity signals with predetermined upper and lower values for evaluation purposes.

6. Process according to claim 1, wherein during the step of scanning at least two measuring beams are used which are positioned at different distances from the bottom of the bottle.

7. Process according to claim 1, wherein during the step of scanning the measuring beam scans the bottle bottom in a circular path.

* * * * *